United States Patent [19]

Sugimoto et al.

[11] Patent Number: 4,604,339

[45] Date of Patent: Aug. 5, 1986

[54] METHOD OF DEVELOPING SILVER HALIDE PHOTOGRAPHIC LIGHT-SENSITIVE MATERIAL

[75] Inventors: Tadao Sugimoto; Hideo Ikeda; Hiroyuki Mifune; Koki Nakamura, all of Kanagawa, Japan

[73] Assignee: Fuji Photo Film Co., Ltd., Kanagawa, Japan

[21] Appl. No.: 556,667

[22] Filed: Nov. 30, 1983

[30] Foreign Application Priority Data

Nov. 30, 1982 [JP] Japan ............................ 57-210498

[51] Int. Cl.[4] ........................ G03C 5/54; G03C 5/24
[52] U.S. Cl. ................................ 430/244; 430/445; 430/448; 430/600; 430/611; 430/251; 430/248
[58] Field of Search ............... 430/445, 600, 611, 448, 430/244, 251, 248

[56] References Cited

U.S. PATENT DOCUMENTS

| | | |
|---|---|---|
| 2,933,388 | 4/1960 | Knott ................................ 430/445 |
| 2,996,382 | 8/1961 | Luckey et al. ...................... 430/502 |
| 3,367,778 | 2/1968 | Berriman ........................... 430/411 |
| 3,826,654 | 7/1974 | Weiss et al. ........................ 430/445 |

Primary Examiner—Won H. Louie
Attorney, Agent, or Firm—Sughrue, Mion, Zinn, Macpeak, and Seas

[57] ABSTRACT

A method of developing silver halide photographic material which contains a light-sensitive silver halide emulsion and an internally-fogged silver halide emulsion, in which the internally-fogged emulsion has internal fogging nuclei at a depth of $0.02\mu$ or more below the surface of the grains is disclosed. The photographic material is developed in the presence of at least one compound selected from the group consisting of tetraazaindenes containing at least one mercapto group, purines containing at least one mercapto group, triazaindenes containing at least one mercapto group and pentaazaindenes containing at least one mercapto group, to increase photographic speed, contrast and maximum density as well as remove uneven stain.

13 Claims, No Drawings

METHOD OF DEVELOPING SILVER HALIDE PHOTOGRAPHIC LIGHT-SENSITIVE MATERIAL

FIELD OF THE INVENTION

The present invention relates to a novel silver halide photographic light-sensitive material and, more particularly, to a silver halide photographic light-sensitive material which provides images of high contrast and high maximum density with high speed.

BACKGROUND OF THE INVENTION

With photographic images made up of silver, the ratio of optical density of the image to a per unit area amount of image-making silver is termed "covering power". This term is employed as a yardstick for estimating optical efficiency of the image-forming silver. As a general rule, the covering power of a silver halide photographic light-sensitive layer is greater the smaller the size of silver halide grains becomes, and becomes lower the larger the size of the silver halide grains. On the other hand, a photographic light-sensitive material of high sensitivity comprises silver halide emulsions which have a large grain size, since sensitivity of a silver halide emulsion layer becomes generally higher the greater a size of silver halide grains is. Consequently, a photographic light-sensitive material of high sensitivity requires a larger per unit area amount of silver in order to attain a definite height of image density. That is to say, it becomes necessary to incorporate a much larger per unit area amount of silver salt into a photographic light-sensitive material in order to achieve both high sensitivity and desired maximum image density.

One attempt to improve covering power while maintaining high sensitivity involves using various kinds of polymers with coarse-grained silver halide emulsions having high sensitivity, as described in British Pat. Nos. 1,048,057 and 1,039,471, and U.S. Pat. Nos. 3,043,697 and 3,446,618. However, these attempts have an insufficient effect on heightening covering power and weaken the emulsion coats. In particular, when photographic light-sensitive materials provided with emulsion coats having strength weakened by application of such techniques are processed in a currently employed automatic developing machine, such techniques have a counterbalancing disadvantage. More specifically, these techniques cause stains on photographic images due to gelatin which has partially been eluted from weakened emulsion coats into the developing or the fixing solution used. The gelatin sticks to the carrying roller installed in the developing machine and is transferred from the carrying roller onto other photographic light-sensitive materials.

As another attempt to obtain photographic images having both high contrast and high covering power with high photographic speed, there are proposed in U.S. Pat. Nos. 2,996,382 and 3,178,282 silver halide photographic light-sensitive materials which contain a coarse-grained silver halide emulsion having high surface sensitivity and a fine-grained silver halide emulsion having fogging nuclei inside the grains in the same layer or in separate layers, which are adjacent to each other.

However, such photographic materials suffer from the defect that development fog tends to be caused therein. Additionally, when those photographic materials are passed through a fixing bath directly after passage through a developing bath without being passed through a stop bath by the use of, e.g., an automatic developing machine or so on, generation of uneven stain comes into question.

Incidentally, as a method for eliminating fog is described in U.S. Pat. No. 3,397,987. The patent discloses a technique wherein heterocyclic nitrogen-containing compounds having a mercapto functional group (e.g., mercaptoazoles) are caused to be held by adsorption on the surface of internally fogged nuclei. However, the uneven stain produced when photographic materials are processed without using any stop bath cannot be reduced with this technique.

Automatic developing machines are now extensively used. Accordingly, it has been increasingly important to prevent the above-described uneven stains.

SUMMARY OF THE INVENTION

It is, therefore, an object of the present invention to provide a silver halide photographic light-sensitive material which has high sensitivity and produces images of high contrast and high maximum density, and to provide a method of developing said sensitive material.

Another object of the present invention is to reduce the generation of developing fog and to provide a silver halide photographic light-sensitive material which causes no uneven stains therein and a developing method therefor.

As a result of our various examinations, it has now been found that the above-described objects are attained with the following photographic light-sensitive material.

That is, the present invention comprises a silver halide photographic light-sensitive material which contains a light-sensitive silver halide emulsion and an internally-fogged silver halide emulsion, with the internally-fogged emulsion having internal fogging nuclei inside the grains at a depth of $0.02\mu$ or more below the surface of the grains, which is developed in the presence of at least one compound selected from the group consisting of tetraazaindenes containing at least one mercapto group, purines containing at least one mercapto group, triazaindenes containing at least one mercapto group and pentaazaindenes containing at least one mercapto group.

DETAILED DESCRIPTION OF THE INVENTION

Uneven stain which is generated by developing a photographic light-sensitive material containing both light-sensitive silver halide emulsions and internally-fogged silver halide emulsions becomes conspicuous when the photographic material is processed passing it through a fixing bath directly after the conclusion of development without passing it through a stop bath, especially by the use of an automatic developing machine.

Such a phenomenon is believed to be caused by interaction of a developing solution with a fixing solution containing sodium thiosulfate or the like, and the extent of uneven stain can be evaluated as well, for instance, by measuring the density of fog which appears when a photographic material is processed with a developing solution prepared by adding a thiosulfate to an ordinary developing solution.

By the way, generation of such uneven stain, as has been stated, could not be prevented by only adding to a photographic light-sensitive material a heterocyclic nitrogen-containing compound having a mercapto group, such as mercaptotetrazoles described in U.S. Pat. No. 3,397,987.

On the other hand, it has been found that the uneven stain can be eliminated in a way by burying internal fogging nuclei in a deep position below the surface of internally-fogged grains. However, a question arises as to how to obtain photographic images having desired photographic characteristics, that is, high photographic speed, high contrast and high maximum density.

According to our invention, the problems described above can be solved by using an internally-fogged emulsion having internal fogging nuclei in a specified depth and carrying out development-processing in the presence of a specified compound.

Desirable compounds which are to be employed in the present invention include those having the following general formulae. That is, tetraazaindenes represented by the general formulae (I), (II) and (III), purines represented by the general formula (IV), triazaindenes represented by the general formula (V) and pentaazaindenes represented by the general formula (VI) are preferably used:

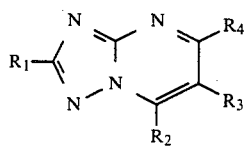
(I)

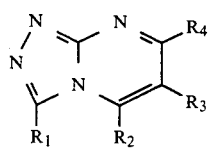
(II)

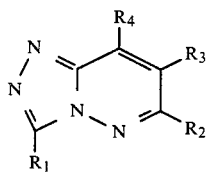
(III)

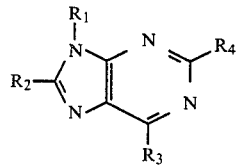
(IV)

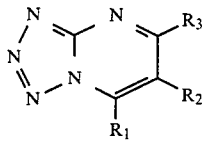
(V)

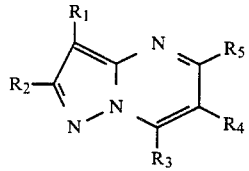
(VI)

Substituents $R_1$ to $R_5$ in the above-illustrated general formula (I) to (VI) include a hydrogen atom, alkyl groups (preferably those having 1 to 20 carbon atoms, such as methyl, ethyl, propyl, octyl, dodecyl, t-butyl, isopropyl, etc.), aryl groups (preferably those having 6 to 20 carbon atoms, such as phenyl, naphthyl, etc.), aralkyl groups (preferably those having 7 to 20 carbon atoms, such as benzyl, phenylethyl, diphenylmethyl, etc.), amino groups, hydroxyl groups, alkoxy groups (preferably those having 1 to 20 carbon atoms, such as methoxy, ethoxy, butoxy, isobutoxy, hexyloxy, etc.), alkoxycarbonyl groups (e.g., ethoxycarbonyl, etc.), cyano groups and mercapto groups. In addition, each of the above-described compounds must have a mercapto group as at least one of its substituents. Further, some of the substituents $R_1$ to $R_5$ may combine with one another and form a ring (e.g., a benzene ring, a naphthalene ring, etc.).

Alkyl groups, aryl groups, aralkyl groups, amino groups, alkoxy groups and so on which are represented by the substituents $R_1$ to $R_5$ may be further substituted with a certain substituent, for example, an amino group, a substituted amino group (e.g., diethylamino, etc.), a hydroxyl group, an alkoxyl group (preferably those having 1 to 5 carbon atoms, such as methoxy, ethoxy, butoxy, etc.), an alkylmercapto group (preferably those having 1 to 5 carbon atoms, such as mercaptomethyl, mercaptopropyl, etc.) or so on.

Specific examples of the compounds which can be employed in the present invention are illustrated below.

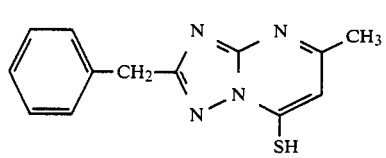
Compound 1

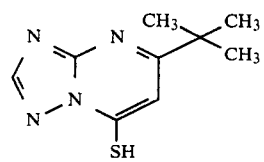
Compound 2

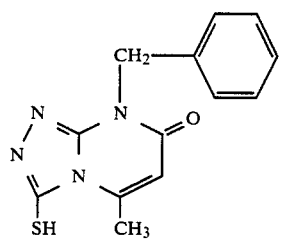
Compound 3

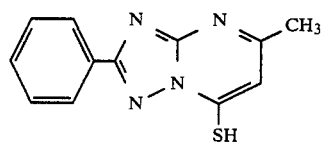
Compound 4

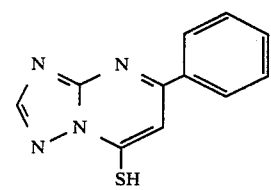
Compound 5

-continued
Compound 6
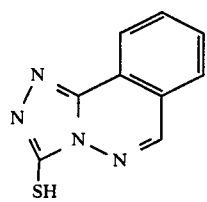
Compound 7
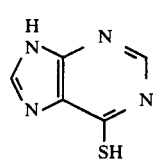
Compound 8
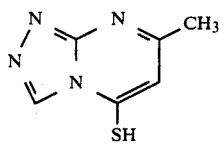
Compound 9
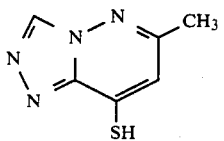
Compound 10
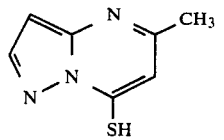
Compound 11
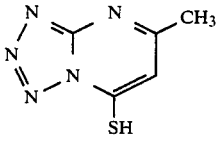
Compound 12
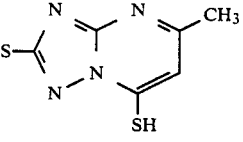
Compound 13
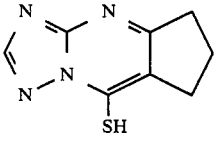
Compound 14
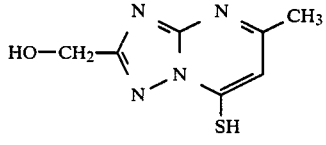
Compound 15
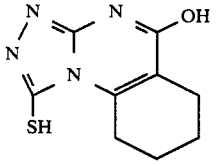
-continued
Compound 16
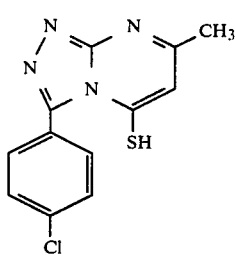
Compound 17
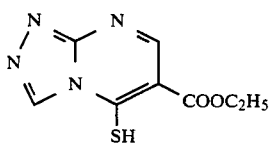
Compound 18
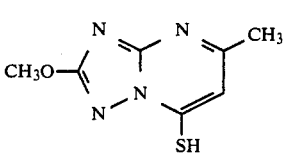
Compound 19
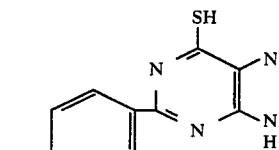
Compound 20
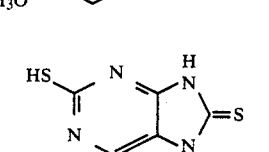
Compound 21
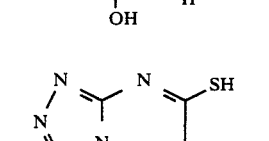
Compound 22
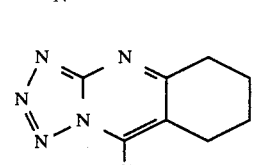
Compound 23
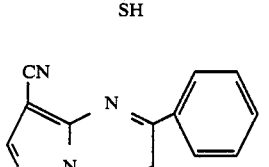
Compound 24
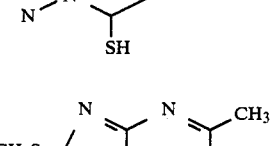
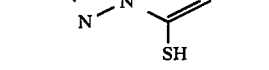

-continued

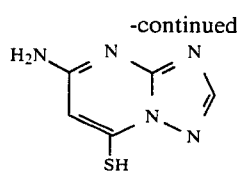
Compound 25

Mercaptoazaindenes to be employed in the present invention are known compounds and can be easily prepared from hydroxyazaindenes. Namely, they can be generally obtained by chlorinating hydroxyazaindenes with a halogenating agent such as phosphorus oxychloride or the like and then by driving thiol compounds from the chlorinated ones using a sulfur compound like thiourea or so on.

The synthesis of the mercaptotetraazaindenes of the present invention are illustrated in the following synthesis examples. Mercaptotetraazaindenes other than those described below can be also synthesized with ease according to the synthetic processes illustrated below.

SYNTHESIS EXAMPLE 1

Synthesis of 4-Mercapto-6-t-butyl-1,3,3a,7-tetraazaindene (Compound 2)

(1) Synthesis of 4-Chloro-6-t-butyl-1,3,3a,7-tetraazaindene

The mixture of 20 g of 4-hydroxy-6-t-butyl-1,3,3a,7-tetraazaindene and 80 ml of phosphorus oxychloride was refluxed over an oil bath at 140° to 150° C. for 3 to 4 hours. Excess phosphorus oxychloride was distilled away under reduced pressure and then the reaction mixture was poured into ice water. The product was extracted with methylene chloride, and dried over anhydrous sodium sulfate. Upon distilling off the methylene chloride, pale yellow crystal in yield of 16 g was obtained.

(2) Synthesis of 4-Mercapto-6-t-butyl-1,3,3a,7-tetraazaindene 8.7 g of thiourea was dissolved in 150 ml of ethanol and thereto was added 4-chloro-6-t-butyl-1,3,3a,7-tetraazaindene. The resulting mixture was refluxed for 1.5 hours over a water bath. At the conclusion of the refluxing the product precipitated as crystals. Upon distilling off the ethanol, needle crystals were obtained. Repeated recrystallization from 1.8 l of ethanol gave 7.4 g of intended compound having a melting point of 285° to 286° C.

Compounds having a thio group on their triazole ring can be synthesized as well according to the process as illustrated below.

SYNTHESIS EXAMPLE 2

Synthesis of 1,2,4-Triazolo[3,4-a]phthalazine-3-thiol (Compound 6)

25 g of 1-hydradinophthalazine was dissolved in pyridine and thereto, 13 g of carbon disulfide was added dropwise at 0° C. After 30 minutes' stirring, it was heated up to 50° C., and the stirring was further continued for 1 hour. Once again the temperature was cooled to 0° C., and excess triethylamine was added dropwise to the reaction system. Thereupon, generation of hydrogen sulfide gas commenced. The reaction mixture was heated under reflux for 3 hours and as a result thereof, generation of the gas stopped. Upon cooling the reaction system crystals separated out. These were filtered off, and recrystallized from ethanol. The yield was 23 g, and the melting point was 270° to 280° C.

The compounds of the present invention can be used independently or in combination of two or more thereof. When incorporated in a sensitive material, the compound of the present invention can be employed in an amount of $1 \times 10^{-5}$ to $1 \times 10^{-1}$ mole and more desirably in an amount of $1 \times 10^{-4}$ to $1 \times 10^{-2}$ mole, per mole of internally-fogged grains. The most advantageous addition amount is around saturated adsorption amount on the surface of internally-fogged grains. Upon adding, the compound of the present invention may be dispersed directly into a hydrophilic colloid, or it may be dissolved in advance in an organic solvent such as methanol, ethylene glycol, etc., and then added in a hydrophilic colloid. The resulting dispersion may be added to at least either a light-sensitive silver halide emulsion or an internally-fogged emulsion, or to both of them, or to the mixture thereof. Of these cases, it is more effective to add in advance to the internally-fogged emulsion. In addition, it is possible to incorporate the compound in a hydrophilic colloidal layer (e.g., a protective layer), an interlayer or the like.

In case of adding to a processing solution, the compound of the present invention may be added to a developing bath, a prebath of the developing bath, or so on. A preferable addition amount of the compound ranges from $10^{-5}$ to $10^{-1}$ mole/l and more particularly from $10^{-4}$ to $10^{-2}$ mole/l.

The term "sensitive" in the present invention means that sensitivity of the light-sensitive silver halide emulsion is higher than that of the internally-fogged silver halide emulsion. More specifically, it means that the light-sensitive silver halide emulsion has sensitivity higher than that of the internally-fogged silver halide emulsion by a factor of 10 or more and preferably 100 or more.

The term "sensitivity" used in the present invention is defined in a similar way as the sensitivity described below.

Examples of light-sensitive silver halide emulsions which can be used in the present invention include usual silver halide emulsions, such as emulsions of the kind which form at the surface of the grains latent image to a very appreciable extent.

More specifically, the emulsions of the kind which form latent image at the surface of the grains comprise those which, when exposed to light for a fixed time between 0.01 and 1 second and developed according to the surface development process (A) as hereinafter described, have a sensitivity greater than the sensitivity attained by exposing the same emulsion to light for the same time described above and developing it according to the internal development process (B) as hereinafter described. In particular, those which have the former sensitivity greater than the latter sensitivity by a factor of 2 or above are advantageous. The sensitivity used herein is defined as follows:

$$S = 100/Eh$$

wherein S means a sensitivity, and Eh represents an exposure required for obtaining the exactly middle density between the maximum density ($D_{max}$) and the minimum density ($D_{min}$), that is, $\frac{1}{2}(D_{max} + D_{min})$.

Surface Development Process (A)

An emulsion to be examined is developed at 20° C. for 10 minutes using a developing solution having the following formula.

N-Methyl-p-aminophenol (hemisulfate): 2.5 g
Ascorbic Acid: 10 g
Sodium Metaborate Tetrahydrate: 35 g
Potassium Bromide: 1 g
Water to make: 1 l

Internal Development Process (B)

An emulsion to be examined is processed at about 20° C. for 10 minutes in a bleaching solution containing 3 g/l of hexacyanoferrate (III) and 0.0126 g/l of phenosafranine and then washed with water for 10 minutes and thereafter processed with a developing solution prepared according to the following formula at 20° C. for 10 minutes.

N-Methyl-p-aminophenol (hemisulfate): 2.5 g
Ascorbic Acid: 10 g
Sodium Metaborate Tetrahydrate: 35 g
Potassium Bromide: 1 g
Sodium Thiosulfate: 3 g
Water to make: 1 l Specific examples of emulsions of the kind which can form latent image at the surface of the grains which can be used herein include silver chloroiodide, silver iodobromide, silver chloride, silver chlorobromide, silver bromide and silver chloroiodobromide. Of these silver halides, those containing an iodide content of 0.1 to 30 mol%, particularly 0.5 to 10 mol%, are especially useful in the present invention. It is desirable that a mean size of the emulsion of the kind which forms latent image at the surface of the grains is greater than that of the silver halide emulsion having fogging nuclei inside the grains, and preferably greater than 0.6 μm. The grain size distribution thereof may be either narrow or broad.

The silver halide grains in the emulsions may have a regular crystal form, such as that of a cube or an octahedron; an irregular crystal form, such as that of a sphere, a plate or so on; or a composite form thereof. A mixture of various crystal forms of silver halide grains may also be present.

Photographic emulsions which can be used in the present invention can be prepared using various methods, as described in, for example, P. Glafkides, *Chimie et Phisique Photographique*, Paul Montel, Paris (1967), G. F. Duffin, *Photographic Emulsion Chemistry*, The Focal Press, London (1966) and V. L. Zelikman et al., *Making and Coating Photographic Emulsion*, The Focal Press, London (1964). More specifically, any of methods, for example, the acid process, the neutral process, the ammonia process and so on may be employed for the first ripening. As the method for reacting a water-soluble silver salt with a water-soluble halide, mention may be made of a single jet method, a double jet method or a combination thereof.

Also, a method in which silver halide grains are produced in the presence of excess silver ion (the so-called reverse mixing method) can be employed in this invention. On the other hand, the so-called controlled double jet method, in which the pAg of the liquid phase wherein silver halide grains are to be precipitated is maintained constant, may be also employed herein.

According to the above-described method, silver halide emulsions having a regular crystal form and being nearly uniform in grain size can be obtained.

Two or more of silver halide emulsions prepared separately may be used in a mixture.

In a process of producing silver halide grains or allowing the produced silver halide grains, to ripen physically, cadmium salts, zinc salts, thallium salts, iridium salts or complexes, rhodium salts or complexes, iron salts or complexes and/or the like may be present.

Removal of the soluble salts from the silver halide emulsions to be used in the present invention is generally carried out after the production of the silver halide grains or after the physical ripening step. The removal can be effected by using the well-known noodle washing method which comprises gelling the gelatin, or using a flocculation method taking advantage of a sedimenting agent such as a polyvalent anion-containing inorganic salt (e.g., sodium sulfate), an anionic surface active agent or an anionic polymer (e.g., polystyrene sulfonic acid), or a gelatin derivative (e.g., an aliphatic acylated gelatin, an aromatic acylated gelatin, an aromatic carbamoylated gelatin or the like). The removal of soluble salts from the silver halide emulsion may be omitted.

The silver halide emulsions to be used in the present invention are, in general, chemically sensitized, though the silver halide emulsions unsensitized chemically (the so-called unafter-ripened emulsions) can be also employed. Conventionally employed chemical sensitization techniques which can be used herein include those which are described in P. Glafkides, *Chimie Photographique*, supra, V. L. Zelikman et al., *Making and Coating Photographic Emulsion*, supra, and H. Frieser, *Die Grundlagen der Photographischen Prozesse mit Silberhalogeniden*, Akademische Verlagsgesellschaft, (1968).

More specifically, sulfur sensitization techniques using compounds containing sulfur reactive with silver ions, and active gelatin; reduction sensitization techniques using reduction compounds; noble metal sensitization techniques using gold or other noble metal compounds; and so on can be used individually or in combination thereof. Suitable sulfur sensitizers include thiosulfates, thioureas, thiazoles, rhodanines and so on, and specific examples of these compounds are described in, for example, U.S. Pat. Nos. 1,574,944, 2,410,689, 2,278,947, 2,728,668, 3,656,955, 4,032,928 and 4,067,740. Suitable reduction sensitizers which can be used herein include stannous salts, amines, hydrazine derivatives, formamidinesulfinic acid, silane compounds and so on. Specific examples of these compounds are described in, for example, U.S. Pat. Nos. 2,487,850, 2,419,974, 2,518,698, 2,983,609, 2,983,610, 2,694,637, 3,930,867 and 4,054,458. For the purpose of the noble metal sensitization, gold complexes and complexes of Group VIII metals such as platinum, iridium, palladium and so on can be employed, and specific examples thereof are described in, for example, U.S. Pat. Nos. 2,399,083 and 2,448,060, British Pat. No. 618,061, and so on.

In the photographic light-sensitive material of the present invention, various kinds of hydrophilic colloids can be used as a binder.

Suitable colloids which can be used for this purpose include gelatin, colloidal albumin, polysaccharides, cellulose derivatives, synthetic resins such as polyvinyl compounds including polyvinyl alcohol derivatives, acrylamide polymers and so on, and other hydrophilic colloids employed conventionally in the photographic art. In addition, hydrophobic colloids, such as polymerized vinyl compound dispersions, especially such dispersions as to increase dimensional stability of photographic materials, can be incorporated together with the hydrophilic colloids. Suitable examples of the compounds of the above-described kind include water-insoluble polymers obtained by polymerizing vinyl monomers such as alkylacrylates or alkylmethacrylates, acrylic acid, sulfoalkylacrylates or sulfoalkylmethacrylates, and/or so on.

The above-described photographic emulsions can contain a wide variety of compounds for purposes of preventing lowering of sensitivity or fogging during production, storage or processing of the resulting photographic materials. Namely, a great number of compounds, for example, not only 4-hydroxy-6-methyl-1,3,3a,7-tetraazaindene, 3-methylbenzothiazole and 1-phenyl-5-mercaptotetrazole, but also many heterocyclic compounds, mercury-containing compounds, mercapto compounds, metal salts and so on, have been well known as those effecting the above-described purposes.

Specific examples of the compounds usable for the above-described purposes are described in K. Mees, *The Theory of the Photographic Process*, 3rd Edition (1966), and U.S. Pat. Nos. 1,758,576, 2,110,178, 2,131,038, 2,173,628, 2,697,040, 2,304,962, 2,324,123, 2,394,198, 2,444,605, 2,444,606, 2,444,607, 2,444,608, 2,566,245, 2,694,716, 2,697,099, 2,708,162, 2,728,663, 2,728,664, 2,728,665, 2,476,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,668 and 3,622,339, British Pat. Nos. 893,428, 403,789, 1,173,609 and 1,200,188, and so on.

Silver halide emulsions having fogging nuclei inside the grains which are to be employed in the present invention are illustrated in detail below. such emulsions comprise those which, when examined by coating the emulsion at a coverage of, e.g., 2 g of silver per square meter on a transparent support and developing it for 2 minutes at 25° C. In D-19 (the developer specified by Eastman Kodak Co.) without exposing it to light, have a transmission fog density of 0.5 or below (exclusive of a fog density of the support itself) and that, when examined by developing the same emulsion for 2 minutes at 35° C. in a developer prepared by adding 0.5 g/l of potassium bromide to D-19 without exposing it to light, have a transmission fog density of 1.0 or above (exclusive of the fog density of the support itself).

The silver halide emulsions having fogging nuclei inside the grains can be made using various known methods. Suitable fogging methods include a method of irradiating silver halide grains with light or X-rays, a method of producing fogging nuclei chemically using reducing agents, gold compounds or sulfur-containing compounds, a method of making silver halide emulsions under low pAg and high pH values, and so on. As a method of producing fogging nuclei only inside the grains, there may be employed the process of fogging at first both the interior and the surface of the silver halide grains using the above-described fogging methods and then bleaching the fogging nuclei present at the surface of the grains in a hexacyanoferrate (III) solution or the like, but it is more preferable to employ the process of preparing at first a core emulsion having fogging nuclei using the process of carrying out the preparation under low pAg and high pH values or the chemically fogging process and then covering the core grains with shell grains. Such a core-shell emulsion as described above can be prepared using known methods, and for the practice of the preparation descriptions in, for example, U.S. Pat. No. 3,206,313 can be referred to.

The depth at which internally-fogged nuclei are present below the surface of the grains can be controlled with ease, e.g., by changing conditions for bleaching fogging nuclei present in the surface part of the grains with a hexacyanoferrate (III) solution or the like (e.g., time, temperature, concentration of the bleaching solution, etc.). On the other hand, in the case of the core-shell emulsion, the position of internal fogging nuclei can be easily controlled by changing the amount of the shell emulsion (in other words, the thickness of the shell).

The internally-fogged grains have internal fogging nuclei at a depth of on the average $0.02\mu$ or more, more preferably on the average $0.04\mu$ or more, below the surface thereof. Namely, it is desired that internal fogging nuclei be burried in the grains so deeply that uneven stain may not be generated upon processing the sensitive material by passing through a fixing bath directly after passage through a developing bath without passage through a stop bath.

The silver halide emulsion having fogging nuclei inside the grains has a smaller mean grain size than the silver halide emulsion of the kind which forms latent image at the surface of the grains. More specifically, good results are obtained when the internally fogged grains has a mean grain size of 1.0 to 0.05 $\mu$m, preferably 0.6 to 0.1 $\mu$m, and more particularly 0.5 $\mu$m or less.

The term grain size of silver halide in the present invention refers to the diameter of grains when they have a spherical or a nearly spherical form, whereas when the grains have another form (e.g., a cubic form, a plate form, etc.), it refers to the diameter of the sphere having the same volume.

Suitable examples of silver halide which can constitute the internally-fogged silver halide emulsion include silver bromide, silver iodobromide, silver iodochlorobromide, silver chlorobromide, silver chloride and any other silver halides.

In the silver halide photographic light-sensitive material of the present invention, a ratio of the content of light-sensitive silver halide to that of internally-fogged silver halide can be changed depending on the kind of the emulsions used (e.g., halide composition), the kind of the sensitive material used and the usage thereof, the contrast of the emulsion used, and so on. However, it is advantageous that the ratio ranges from 100:1 to 1:100, especially from 10:1 to 1:10.

The sensitive material of the present invention can be further improved in photographic characteristics (specifically increased in sensitivity, or so on) by incorporating a compound represented by the following formula in any of the constituent elements provided on the support:

wherein A and B may be the same as or different from each other, and they each represents an alkyl group, an aralkyl group, an aryl group, a heterocyclic group, or

where R represents an alkyl group, an aryl group, an aralkyl group, a heterocyclic group or an amino group.

As examples of such a compound, mention may be made of:

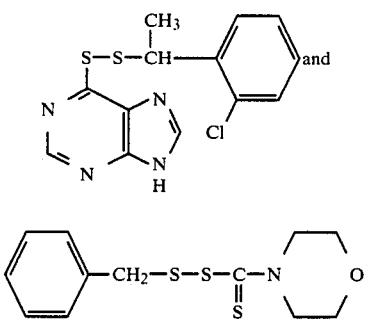

As for the layer structure of the photographic material of the present invention, there can be thought out some preferred embodiments. For example, (1) a layer structure such that a coating composition containing both light-sensitive silver halide grains and internally fogged grains containing at least one compound of the present invention is coated on a support; (2) a layer structure such that an emulsion containing internally-fogged grains which are adsorbed by at least one compound of the present invention is firstly coated on a support and further thereon an emulsion containing light-sensitive silver halide grains is coated; (3) a layer structure such that firstly light-sensitive silver halide grains, at least one compound of the present invention and internally-fogged grains are incorporated in the same coating composition (emulsion), the resulting coating composition is coated on a support and thereon an emulsion containing light-sensitive silver halide grains is further coated; (4) a layer structure such that light-sensitive silver halide grains and an internally-fogged grain emulsion containing at least one compound of the present invention are incorporated in the same coating composition (emulsion), and coated on a support and further thereon an emulsion containing both light-sensitive silver halide grains and an internally-fogged grain emulsion containing at least one compound of the present invention, which has a composition different from that of the lower layer, is coated; and (5) an embodiment such that one of the layer structures (1) to (4) from which the compound of the present invention is removed, though it may not be removed therefrom, is employed and that, the compound of the present invention is incorporated in a developing solution to be used may be present.

A protective layer which can be provided in the silver halide photographic light-sensitive material of the present invention is a hydrophilic colloidal layer, and suitable examples of the hydrophilic colloid used therein include the same ones as described hereinbefore. The protective layer may be a single layer or a double layer.

The silver halide photographic light-sensitive material may contain a matting agent and/or a smoothing agent in its emulsion layer or its protective layer, especially in its protective layer. Suitable examples of the matting agent include organic compounds such as water dispersible vinyl polymers like polymethylmethacrylate having a proper particle size (e.g., 0.3 to 5µ, or one which is greater than the thickness of the protective layer by a factor of 2 or above, especially 4 or above), inorganic compounds such as silver halides, barium, strontium sulfate, etc., and so on. The smoothing agent is available for prevention of adhesion troubles, in analogy with the matting agent, and effective for improvement in frictional characteristics influencing the fitness to cameras upon taking or projecting with motion picture films. Specific examples of the smoothing agent include waxes such as liquid paraffin and higher fatty acid esters, polyfluorohydrocarbons and their derivatives, silicones such as polyalkylpolysiloxane, polyarylpolysiloxane, polyalkylarylpolysiloxane and adducts of these siloxanes and alkylene oxides, and so on.

The silver halide photographic light-sensitive material of the present invention may be provided with an antihalation layer, an interlayer, a filter layer and so on, as occasion demands.

The photographic silver halide emulsion layers and other hydrophilic colloidal layers can be hardened using any of suitable hardeners. Examples of these hardeners include vinyl sulfonyl compounds as described in Japanese Patent Application (OPI) Nos. 76025/78, 76026/78 and 77619/78 (the term "OPI" as used herein refers to a "published unexamined Japanese patent application"); active halogen containing hardeners; dioxane derivatives; polysaccharides like oxidized starch; and so on.

To the photographic silver halide emulsion layers can be added other additives, especially those which are useful for the photographic emulsions, for example, lubricants, sensitizers, light-absorbing dyes, plasticizers and so on.

In addition, iodine ion releasing compounds (e.g., potassium iodide, etc.) can be incorporated in the silver halide emulsions of the present invention or in the developing solution to be used, resulting in contribution to the production of desired image.

The sensitive material of the present invention may contain water-soluble dyes in its hydrophilic colloidal layers for various purposes, for example, as a filter dye, prevention of irradiation or halation, and so on. Examples of such dyes include oxonol dyes, hemioxonol dyes, styryl dyes, merocyanine dyes, cyanine dyes and azo dyes. Of these dyes, oxonol dyes, hemioxonol dyes and merocyanine dyes are of greater advantage.

When dyes or ultraviolet absorbents are incorporated in the hydrophilic colloidal layer of the present invention, they may be mordanted by cationic polymers or the like. Examples of polymers which can be used for mordanting include those which are described in British Pat. No. 685,475, U.S. Pat. Nos. 2,675,316, 2,839,401, 2,882,156, 3,048,487, 3,184,309 and 3,445,231, West German Patent Application (OLS) No. 1,914,362, Japanese Patent Application (OPI) Nos. 47624/75 and 71332/75, and so on.

The sensitive material of the present invention may contain surface active agents for various purposes. All types of surface active agents, nonionic, ionic and amphoteric ones, can be used properly according to the purpose for which they are added. Suitable examples of surface active agents which can be used herein include polyoxyalkylene derivatives, amphoteric amino acids (including sulfobetaines) and so on. These surface active agents are described in U.S. Pat. Nos. 2,600,831, 2,271,622, 2,271,623, 2,275,727, 2,787,604, 2,816,920 and 2,739,891, and Belgian Pat. No. 652,862.

The photographic emulsion of the present invention may be spectrally sensitized by sensitizing dyes to blue light having relatively long wavelengths, green light, red light or infrared rays. Suitable examples of sensitizing dyes which can be used include cyanine dyes, merocyanine dyes, complex cyanine dyes, complex merocyanine dyes, holopolar cyanine dyes, styryl dyes, hemicyanine dyes, oxonol dyes, hemioxonol dyes and so on.

Specific examples of sensitizing dyes which can be advantageously employed in the present invention include those which are described in U.S. Pat. Nos. 3,522,052, 3,619,197, 3,715,828, 3,615,643, 3,615,632, 3,617,293, 3,628,964, 3,703,377, 3,666,480, 3,667,960, 3,679,428, 3,672,897, 3,769,062, 3,556,800, 3,615,613, 3,615,638, 3,615,635, 3,705,809, 3,632,349, 3,677,765, 3,770,449, 3,770,440, 3,769,025, 3,745,014, 3,713,828, 3,567,458, 3,625,698, 2,526,632 and 2,503,776, Japanese Patent Application (OPI) No. 76525/73, Belgian Pat. No. 691,807, and so on.

In the present invention also such sensitizing dyes are used in concentrations equal to those which have been employed in conventional negative type silver halide emulsions. In particular, it is advantageous to use them in such concentrations as not to lower substantially the inherent sensitivity of the silver halide emulsions to which they are added. Specifically, preferred concentrations of such sensitizing dyes range from about $1.0 \times 10^{-5}$ to about $5 \times 10^{-4}$ mole, particularly about $4 \times 10^{-5}$ to $2 \times 10^{-4}$ mole, per mole of silver halide.

In the photographic light-sensitive material of the present invention, photographic emulsion layers and other layers are coated on one side or both sides of a conventional flexible support. Suitable examples of the flexible support include films made of cellulose nitrate, cellulose acetate, polyvinyl chloride, polyethylene terephthalate, polycarbonate and other semisynthetic or synthetic polymers, and paper on which a baryta layer or an α-olefin polymer (e.g., polyethylene, propylene, ethylene-butene copolymer, etc.) is coated or laminated. The support may be colored by pigments or dyes. It may be blackened for the purpose of shielding the light. The surface of the support is, in general, subjected to a subbing treatment in order to heighten adhesiveness to photographic emulsions or others. Before or after the subbing treatment, the surface of the support may be submitted to a corona discharge treatment, an ultraviolet irradiation treatment, a flame treatment or so on.

The photographic emulsions and other hydrophilic colloidal layers to constitute the photographic light-sensitive material of the present invention can be coated on a support or other constituent layers using various known coating methods. Examples of the coating method which can be used include a dip coating method, a roller coating method, a curtain method, an extrusion coating method and so on. Among these methods, those which are described in U.S. Pat. Nos. 2,681,294, 2,761,791 and 3,526,528 are of greater advantage.

The present invention can be applied to any of photographic light-sensitive materials which need to have high sensitivity or high contrast. Specific examples of such materials are X-ray photographic materials, lithographic photographic materials, black-and-white negative type photographic materials, color negative photosensitive materials, color paper photosensitive materials and so on.

In addition, the present invention can be also applied to diffusion transfer photographic materials and color diffusion transfer photographic materials, in which positive images are produced by dissolving undeveloped silver halides and depositing them on the image-receiving layer provided in the vicinity of the silver halide emulsion layers.

The sensitive material of the present invention can receive photographic processing using any of known methods and any of known processing solutions, as described in, for example, *Research Disclosure*, No. 176, pages 20–30 (RD-17643). The photographic processing may be either a photographic processing for forming silver image (black-and-white photographic processing) or a photographic processing for forming dye image (color photographic processing), according to the purpose. The processing temperature is usually selected from the range of 18° C. to 50° C. However, it is possible to employ temperatures lower than 18° C. or higher than 50° C.

A developing solution which can be used for black-and-white photographic processing can contain known developing agents. As such developing agents, dihydroxybenzenes (e.g., hydroquinone), 3-pyrazolidones (e.g., 1-phenyl-3-pyrazolidone), aminophenols (e.g., N-methyl-p-aminophenol) and so on can be used individually or in combination thereof. The sensitive material of the present invention can be also development-processed using a developing solution containing imidazoles as the silver halide solvent described in Japanese Patent Application No. 155489/80. Further, the sensitive material can be also processed with a developing solution containing both the silver halide solvent described in Japanese Patent Application No. 136267/81 and such an additive as an indazole or a triazole. In addition to these additives, the developing solution contains generally known preservatives, alkali agents, pH buffers, antifoggants and, optionally, dissolution aids, color toning agents, development accelerators, surface active agents, defoaming agents, water softeners, hardeners, viscosity providing agents and so on.

Furthermore, the so-called "litho-type" development processing can be applied to the photographic emulsion of the present invention. The term "litho-type" development processing refers to the development processing that for the purpose of photographic reproduction of line image or photographic reproduction of halftone image by the use of dots, the development is made to proceed infectiously by using usually dihydroxybenzenes as a developing agent under the condition of a low sulfite ion concentration (which is described in detail in Mason, *Photographic Processing Chemistry*, pages 163 to 165 (1966)).

As a special modification of the development processing, there can be employed the method that a developing agent is incorporated in a sensitive material, for example, in an emulsion layer thereof, and the sensitive material is processed in an alkaline aqueous solution to carry out development. If the developing agent is hydrophobic, it can be incorporated in an emulsion layer using various methods as described in, for example, *Research Disclosure*, No. 169 (RD-16928), U.S. Pat. No. 2,739,890, British Pat. No. 813,253, West German Pat. No. 1,547,763, and so on. The above-described development processing may be carried out in combination with the silver salt stabilizing processing using thiocyanates.

As a fixing solution, those which have generally used compositions can be used in the present invention. Suitable examples of the fixing solution include thiosulfates, thiocyanates, and organic sulfur-containing compounds which have been known to have a fixing effect. The fixing solution may additionally contain water-soluble aluminum salts as a hardener.

EXAMPLE 1

(1) Preparation of Light-Sensitive Silver Halide Emulsion

According to the conventional ammonia process, a silver iodobromide emulsion having a mean grain size of 1.3μ (AgI: 2 mol%) was prepared from silver nitrate, potassium bromide and potassium iodide. The resulting emulsion was subjected to chemical sensitization consisting of gold sensitization using chloroauric acid and sulfur sensitization using sodium thiosulfate and then rinsed using the conventional precipitation process. Thereto, 4-hydroxy-6-methyl-1,3,3a,7-tetraazaindene was added as a stabilizer. Thus, the light-sensitive silver iodobromide emulsion A was obtained.

(2) Preparation of Internally-Fogged Emulsion

In the process of preparing a silver bromide emulsion by adding potassium bromide and a silver nitrate aqueous solution simultaneously to a 2 wt% gelatin aqueous solution kept at 55° C., six kinds of core emulsions differing in grain size were prepared by changing the addition time. Each of the core emulsions was heated up to 75° C. and thereto silver nitrate and sodium hydroxide were added and thereby the resulting emulsion was ripened for 15 minutes to result in fogging chemically the surface of core grains. Thereafter, the pH and the pAg values of the emulsion were changed back to their respective original values by adding thereto acetic acid and potassium bromide and then the temperature of the emulsion was lowered to 55° C. Subsequently, a potassium bromide and a silver nitrate solutions were added simultaneously taking such time as to produce grains having a mean size of 0.370μ. The resulting emulsion was deposited as shell on fogged grains contained in each of the core emulsions, and rinsed by the conventional precipitation method. The thus obtained grains were redispersed into a gelatin solution, resulting in preparation of the following internally-fogged emulsions B-1 to B-6.

| Emulsion No. | Mean Size of Core Grain (μ) | Mean Grain Size (μ) | Mean Thickness of Shell (μ) |
|---|---|---|---|
| B-1 | 0.346 | 0.370 | 0.012 |
| B-2 | 0.340 | 0.370 | 0.015 |
| B-3 | 0.326 | 0.370 | 0.022 |
| B-4 | 0.302 | 0.370 | 0.034 |
| B-5 | 0.290 | 0.370 | 0.040 |
| B-6 | 0.278 | 0.370 | 0.046 |

(3) Preparation of Comparative Samples 1 to 7

The above-described light-sensitive silver halide emulsion A and a gelatin aqueous solution for a protective layer were coated in sequence on the subbing layer provided on a polyethylene terephthalate base film to prepare Comparative Sample 1. Therein, the coverage of the emulsion A was 2.0 g of silver per square meter, the coverage of gelatin of the protective layer was 1.3 g/m², and the coverage of gelatin of the emulsion layer was 2.6 g/m². Next, the emulsion obtained by mixing the light-sensitive silver halide emulsion A with one of the internally-fogged emulsions B-1 to B-6, and a gelatin solution for a protective layer were coated in sequence on the same base to prepare Comparative Samples 2 to 7. Therein, the coverage of silver of the emulsion A was all 2.0 g/m², the coverage of silver of the internally-fogged emulsions B-1 to B-6 each was 2.0 g/m², the coverage of gelatin of the protective layer was 1.3 g/m², and the coverage of gelatin of the emulsion layers each was 2.6 g/m².

(4) Preparation of Samples 8 to 10 of the Present Invention

Compound 1 of the present invention was previously added to the internally-fogged emulsions B-4, B-5 and B-6 in $1.7 \times 10^{-3}$ mole portions per 1 mole of silver halide. Each of the resulting emulsions was mixed with the above-described light-sensitive silver halide emulsion A, coated on the same base as used in comparative samples and further thereon a gelatin solution was coated as a protective layer. Thus, Samples 8 to 10 of the present invention were obtained. Therein, the coverage of silver of the emulsion A was all 2.0 g/m², the coverage of silver of the internally-fogged emulsions B-4 to B-6 each was 2.0 g/m², the coverage of gelatin of the protective layer was 1.3 g/m², and the coverage of gelatin of the emulsion layers each was 2.6 g/m².

(5) Photographic Processing

Each of the thus prepared Samples 1 to 10 was exposed to light through wedge, developed at 35° C. for 25 sec. using the developing solution having the following formula, and subjected to, in sequence, stop, fixing, washing and drying processings. Thereafter, sensitometry of each of the thus processed samples was carried out.

Composition of Developing Solution

Potassium Hydroxide: 29.14 g
Glacial Acetic Acid: 10.96 g
Potassium Sulfite: 44.20 g
Sodium Hydrogencarbonate: 7.50 g
Boric Acid: 1.00 g
Diethylene Glycol: 28.96 g
Ethylenediaminetetraacetic Acid: 1.67 g
5-Methylbenzotriazole: 0.06 g
5-Nitroindazole: 0.25 g
Hydroquinone: 30.00 g
1-Phenyl-3-pyrazolidone: 1.50 g
Glutaraldehyde: 4.93 g
Sodium Metahydrogensulfite: 12.60 g
Water to make: 1 l Results obtained are shown in Table 1.

TABLE 1

| Sample No. | Emulsion | Shell Thickness of Emulsion B (μ) | Additive (mol per mol AgBr of Emulsion B) | Fog Value | Relative* Sensitivity | Maximum Density (Dm) | Gamma |
|---|---|---|---|---|---|---|---|
| Comparison 1 | (A) | — | — | 0.04 | 100 | 0.90 | 0.5 |
| Comparison 2 | (A) + (B-1) | 0.012 | — | 1.68 | 105 | 3.00 | 0.6 |
| Comparison 3 | (A) + (B-2) | 0.015 | — | 0.28 | 130 | 2.70 | 1.5 |
| Comparison 4 | (A) + (B-3) | 0.022 | — | 0.06 | 110 | 1.18 | 0.6 |
| Comparison 5 | (A) + (B-4) | 0.034 | — | 0.06 | 95 | 1.00 | 0.5 |

TABLE 1-continued

| Sample No. | Emulsion | Shell Thickness of Emulsion B (μ) | Additive (mol per mol AgBr of Emulsion B) | Photographic Characteristics | | | |
|---|---|---|---|---|---|---|---|
| | | | | Fog Value | Relative* Sensitivity | Maximum Density (Dm) | Gamma |
| Comparison 6 | (A) + (B-5) | 0.040 | — | 0.05 | 90 | 1.00 | 0.5 |
| Comparison 7 | (A) + (B-6) | 0.046 | — | 0.05 | 85 | 1.00 | 0.5 |
| This Invention 8 | (A) + (B-4) | 0.034 | Compound 1 ($1.7 \times 10^{-3}$) | 0.03 | 150 | 3.10 | 2.2 |
| This Invention 9 | (A) + (B-5) | 0.040 | Compound 1 ($1.7 \times 10^{-3}$) | 0.03 | 145 | 2.85 | 2.1 |
| This Invention 10 | (A) + (B-6) | 0.046 | Compound 1 ($1.7 \times 10^{-3}$) | 0.03 | 140 | 2.80 | 2.0 |

*Relative sensitivity is represented by taking the sensitivity of Sample 1 as 100.

It is apparent from Table 1 that Comparative Samples 2 to 7 which did not contain the additive of the present invention had no intended effects (high sensitivity, high contrast and high Dm) if they did not have a shell thickness of about 0.015μ or less. However, in case of such a thin shell thickness as described above, fog density was increased, and when the shell thickness was about 0.012μ generation of fog was particularly dense. On the other hand, the samples of the present invention 8 to 10 had high sensitivity, high contrast and high Dm and further very low fog density. Namely, the intended effects of the present invention were produced satisfactorily in these Samples 8 to 10.

EXAMPLE 2

(1) Preparation of Samples of the Present Invention 11 to 15

Compounds 2, 3, 4, 5 and 7 of the present invention were previously added to separate portions of the internally-fogged emulsion B-5 described in Example 1 in an amount of $1.7 \times 10^{-3}$ mole per mole of silver halide. Next, each of the resulting emulsion was mixed with the light-sensitive silver halide emulsion A described in Example 1, coated on the subbing layer provided on a polyester base and further thereon a gelatin aqueous solution was coated as a protective layer. Thus, samples of the present invention 11 to 15 were obtained. Therein, the coverage of silver of the emulsion A was all 2.0 g/m², the coverage of silver of the emulsion B-5 was all 2.0 g/m², the coverage of gelatin of the protective layer was 1.3 g/m², and the coverage of gelatin of the emulsion layers each was 2.6 g/m².

(2) Preparation of Comparative Samples 16 and 17

The following comparative compounds in place of the compounds of the present invention were previously added to separate portions of the same internally-fogged emulsion B-5 in an amount of $1.7 \times 10^{-3}$ mole per 1 mole of silver halide.

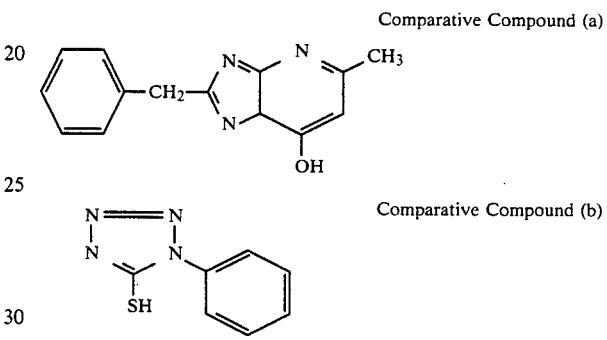

Comparative Compound (a)

Comparative Compound (b)

Subsequently, each of the resulting emulsions was mixed with the same light-sensitive silver halide emulsion A, and coated on the same base. Further, the gelatin aqueous solution was coated on the above-described emulsion coat as a protective layer. Thus, Comparative Samples 16 and 17 were obtained. Therein, the coverage of silver of the emulsion A was all 2.0 g/m², the coverage of silver of the emulsion B-5 was all 2.0 g/m², the coverage of gelatin of the protective layer was 1.3 g/m², and the coverage of gelatin of the emulsion layer was 2.6 g/m².

(3) Photographic Processing

The thus prepared Samples 11 to 15 of the present invention, the Comparative Samples 16 and 17, and the Comparative Samples 1 and 6 and the Sample 9 of the present invention which were prepared in Example 1 were processed in the same manner as described in Example 1, and subjected to sensitometry.

The results obtained are set forth in Table 2.

TABLE 2

| Sample No. | Emulsion | Additive (mol per mol of AgBr of Emulsion B) | Photographic Characteristics | | | |
|---|---|---|---|---|---|---|
| | | | Fog Value | Relative Sensitivity | Maximum Density | Gamma |
| Comparison 1 | (A) | — | 0.04 | 100 | 0.90 | 0.5 |
| Comparison 6 | (A) + (B-5) | — | 0.09 | 90 | 1.00 | 0.5 |
| This Invention 9 | " | Compound 1 ($1.7 \times 10^{-3}$) | 0.03 | 145 | 2.85 | 2.1 |
| This Invention 11 | " | Compound 2 ($1.7 \times 10^{-3}$) | 0.01 | 105 | 2.80 | 1.8 |
| This Invention 12 | " | Compound 3 ($1.7 \times 10^{-3}$) | 0.03 | 140 | 2.80 | 2.0 |
| This Invention 13 | " | Compound 4 ($1.7 \times 10^{-3}$) | 0.01 | 145 | 2.85 | 2.1 |
| This Invention 14 | " | Compound 5 ($1.7 \times 10^{-3}$) | 0.04 | 150 | 2.85 | 2.2 |
| This Invention 15 | " | Compound 7 ($1.7 \times 10^{-3}$) | 0.04 | 150 | 2.90 | 2.2 |

TABLE 2-continued

| Sample No. | Emulsion | Additive (mol per mol of AgBr of Emulsion B) | Fog Value | Relative Sensitivity | Maximum Density | Gamma |
|---|---|---|---|---|---|---|
| Comparison 16 | " | Comparative Compound (a) ($1.7 \times 10^{-3}$) | 0.08 | 90 | 1.00 | 0.5 |
| Comparison 17 | " | Comparative Compound (b) ($1.7 \times 10^{-3}$) | 0.01 | 10 | 0.85 | 0.3 |

As can be apparently seen from Table 2, Samples 9 to 15 which contained the compounds of the present invention produced the intended effects (high sensitivity, high contrast and high maximum density) to the full and had reduced fog, though their shell was thick. On the other hand, the Comparative Samples 16 and 17 to which comparative compounds (a) and (b) were added respectively did not produce the intended effects (high sensitivity, high contrast and high maximum density). Therefore, it has turned out that the additives to be employed in the present invention should have at least one mercapto group and an azaindene nucleus as their mother nucleus.

EXAMPLE 3

(1) Preparation of Comparative Sample 18

Compound 1 of the present invention was previously added to the internally-fogged emulsion B-2, which was described in Example 1, in an amount of $1.7 \times 10^{-3}$ mole per 1 mole of silver halide. Next, the resulting emulsion was mixed with the light-sensitive silver halide emulsion A, which was also described in Example 1, and coated on the subbing layer provided on a polyester base. Further, a gelatin solution was coated on the resulting emulsion coat as a protective layer. Thus, the Comparative Sample 18 was obtained. Therein, the coverage of silver of the emulsion A was 2.0 g/m², the coverage of silver of the emulsion B-2 was 2.0 g/m², the coverage of gelatin of the protective layer was 1.3 g/m², and the coverage of gelatin of the emulsion layer was 2.6 g/m².

(2) Evaluation of Uneven Stain

The Comparative Sample 18, the Comparative Samples 3 to 7, which was prepared in Example 1, and the Samples 8 to 10 of the present invention, respectively, were developed at 35° C. for 25 sec. with a developing solution, which was prepared by adding 7 g/l of $Na_2S_2O_3$ to the developing solution described in Example 1, without receiving any light-exposure treatment. Each of the developed samples was subjected to, in sequence, fixing, rinsing and drying processings. Fog density of the thus processed samples was measured and thereby the degree of uneven stain to be generated was evaluated.

The results obtained are set forth in Table 3.

On the other hand, the Comparative Samples 3 to 7, and 18, and the samples of the present invention 8 to 10, respectively, were exposed to light in the same manner as in Example 1 and then developed at 35° C. for 25 sec. using an automatic developing machine (RN automatic developing machine produced by Fuji Photo Film Co., Ltd.) in which the same developing solution as described in Example 1 was used. Subsequently, each of the samples was subjected to, in sequence, fixing, rinsing and drying processings. As a result of the above-described processings, it has been found that uneven stain was decreased with the decrease in fog value set forth in Table 3, and eventually came to be substantially unobservable when the fog value became 2.0 or less.

Accordingly, the uneven stain was decreased with increase in shell thickness of the internally-fogged emulsion (emulsion B).

The uneven stain was not observed substantially in the samples of the present invention 8 to 10 and, at the same time, image of high sensitivity, high contrast, high maximum density and very low fog density was obtained therein. In addition, if the shell thickness was thin, the addition of the compounds of the present invention had no effect on reduction of the uneven stain, as can be seen from the result of the Sample 18. In the Samples 6 and 7 also, the uneven stain was not observed substantially. However, as demonstrated in Example 1, the intended sensitivity, maximum dneisyt and gamma were not attained therein.

EXAMPLE 4

(1) Preparation of Samples of the Present Invention 19 and 20

Compound 1 of the present invention was previously added to the internally-fogged emulsion B-5, which was described in Example 1, in an amount of $1.7 \times 10^{-3}$ mole per 1 mole of silver halide. Next, the resulting emulsion was mixed with the light-sensitive silver halide emulsion A. The mixed emulsion, the emulsion A alone, and a gelatin aqueous solution for the protective layer were coated successively on the subbing layer provided on a polyester base to obtain Sample 19. Separately, the following Compound (c) was added to the emulsion, which was prepared by mixing the above-described emulsion to which Compound 1 was added in advance

TABLE 3

| Sample No. | Emulsion | Shell Thickness of Emulsion B (μ) | Additive (mol per mol of AgBr of Emulsion B) | Fog Density due to Processing* |
|---|---|---|---|---|
| Comparison 3 | (A) + (B-2) | 0.015 | — | 2.7 |
| Comparison 4 | (A) + (B-3) | 0.022 | — | 2.6 |
| Comparison 5 | (A) + (B-4) | 0.034 | — | 2.2 |
| Comparison 6 | (A) + (B-5) | 0.040 | — | 1.8 |
| Comparison 7 | (A) + (B-6) | 0.046 | — | 1.6 |
| Comparison 18 | (A) + (B-2) | 0.015 | Compound 1 ($1.7 \times 10^{-3}$) | 2.8 |
| This Invention 8 | (A) + (B-4) | 0.034 | Compound 1 ($1.7 \times 10^{-3}$) | 2.0 |
| This Invention 9 | (A) + (B-5) | 0.040 | Compound 1 ($1.7 \times 10^{-3}$) | 1.6 |
| This Invention 10 | (A) + (B-6) | 0.046 | Compound 1 ($1.7 \times 10^{-3}$) | 1.5 |

*Processing carried out using the developer to which $Na_2S_2O_3$ was added.

with the above-described light-sensitive silver halide emulsion A, in an amount of $8.6 \times 10^{-4}$ mole per 1 mole of the mixed silver halide.

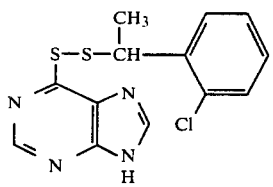

Compound (c)

Next, the resulting emulsion, the emulsion A alone, and a gelatin aqueous solution for the protective layer were coated successively on the subbing layer provided on a polyester base to obtain the Sample 20. In the Samples 19 and 20, the coverage of silver of the emulsion B-5 was 0.7 g/m², the coverage of silver of the emulsion A in the lower emulsion layer was 0.7 g/m² and that in the upper emulsion layer was 2.0 g/m², the coverage of gelatin of the protective layer was 1.3 g/m², and the total coverage of gelatins of the emulsion layers was 2.2 g/m².

(2) Preparation of Comparative Sample 21

The emulsion prepared by mixing the internally-fogged emulsion B-5, which was described in Example 1, with the light-sensitive silver halide emulsion A, the emulsion A alone and a gelatin aqueous solution for the protective layer were coated successively on the subbing layer provided on a polyester base to obtain the Comparative Sample 21. Therein, the coverage of silver of the emulsion B-5 was 0.7 g/m², the coverage of silver of the emulsion A in the lower layer was 0.7 g/m² and that in the upper layer was 2.0 g/m², the coverage of gelatin of the protective layer was 1.3 g/m², and the total coverage of gelatins of the emulsion layers was 2.2 g/m².

Each of the thus obtained Samples 19, 20 and 21 was exposed to light in the same manner as described in Example 1, developed at 35° C. for 25 sec. with the same developing solution as used in Example 1 using the automatic developing machine (RN automatic developing machine) and subsequently, fixed, rinsed and dried. Sensitometry of the images obtained was carried out to obtain results shown in Table 4.

sults, the present invention was also effective in such a layer structure as in Samples 19 to 21. In addition, more desirable photographic characteristics are obtained by the combined use of the compound of the present invention and such a compound as Compound (c).

EXAMPLE 5

Two portions of Sample 6 described in Example 1 were exposed to light in the same manner as in Example 1, and developed separately. One portion was processed at 35° C. for 25 sec. using the same developing solution as described in Example 1 in the automatic developing machine (RN developing machine). The other portion was processed with a different developing solution, which was prepared by adding the compound of the present invention to the developing solution described in Example 1 in an amount of $1 \times 10^{-3}$ mole per liter of the developing solution, under the same developing condition. Subsequently, each of the resulting portions was subjected, in sequence, to fixation, rinsing, drying and sensitometry.

Results obtained are shown in Table 5.

TABLE 5

| Sample No. | Additive in Developing Solution (addition amount per liter) | Photographic Characteristics | | | |
|---|---|---|---|---|---|
| | | Fog Value | Relative* Sensitivity | Maximum Density | Gamma |
| Comparison 6 | — | 0.09 | 100 | 1.0 | 0.5 |
| This Invention 6 | Compound 1 ($1 \times 10^{-3}$ mole) | 0.06 | 125 | 1.5 | 1.0 |

*Relative sensitivity represented by taking the case, in which the developing solution free from the additive of the present invention is used, as 100.

No uneven stains were observed on these samples.

Accordingly, the intended results were found to be produced only if the compounds of the present invention were present at the time of development, whether they were in the film or in the developing solution.

While the invention has been described in detail and with reference to specific embodiments thereof, it will be apparent to one skilled in the art that various changes and modifications can be made therein without departing from the spirit and scope thereof.

What is claimed is:

1. A method of developing, after imagewise exposure, a silver halide photographic light-sensitive material which contains a light-sensitive silver halide emulsion and an internally-fogged silver halide emulsion, comprising: providing as said internally-fogged emulsion an emulsion having internal fogging nuclei inside the grains at a depth of 0.02μ or more below the surface of the grains, and developing said photographic light-sensitive material in the presence of a compound selected from the group consisting of tetraazaindenes containing at least one mercapto group, purines containing at least one mercapto group, triazaindenes containing at least one mercapto group and pentaazain-

TABLE 4

| Sample No. | Additive | Photographic Characteristics | | | |
|---|---|---|---|---|---|
| | | Fog Value | Relative* Sensitivity | Maximum Density | Gamma |
| Comparison 21 | — | 0.03 | 100 | 1.10 | 0.7 |
| This Invention 19 | Compound 1 | 0.01 | 120 | 1.90 | 2.0 |
| This Invention 20 | Compound 1 + Compound (c) | 0.01 | 135 | 2.00 | 3.5 |

*Relative sensitivity represented by taking the sensitivity of Sample 21 as 100.

No uneven stains were observed on these samples. As can be apparently seen from the above-described redenes containing at least one mercapto group, thereby obtaining a negative image.

2. A method of developing a silver halide photographic light-sensitive material as claimed in claim 1, wherein the compound is selected from the group consisting of tetraazaindenes represented by the general formulae (I), (II) and (III), purines represented by the general formula (IV), triazaindenes represented by the general formula (V) and pentaazaindenes represented by the general formula (VI):

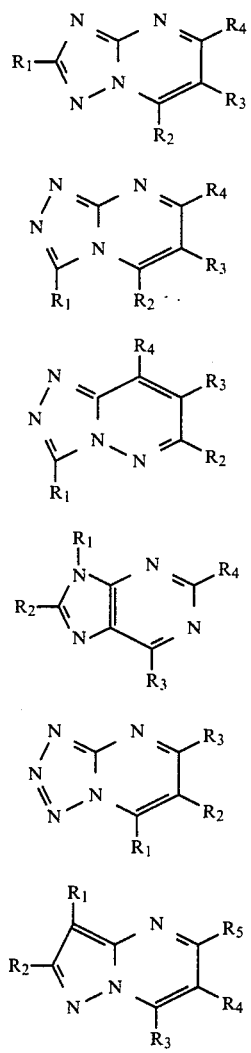

wherein $R_1$ to $R_5$ represent a hydrogen atom, an alkyl group containing 1 to 20 carbon atoms, an aryl group containing 6 to 20 carbon atoms, an aralkyl group containing 7 to 20 carbon atoms, an amino group, a hydroxyl group, an alkoxy group containing 1 to 20 carbon atoms, an alkoxycarbonyl group, a cyano group, and a mercapto group; and at least one of $R_1$, $R_2$, $R_3$ and $R_4$ in the general formulae (I), (II), (III) and (IV) represents a mercapto group; at least one of $R_1$, $R_2$ and $R_3$ in the general formula (V) represents a mercapto group; and at least one of $R_1$, $R_2$, $R_3$, $R_4$ and $R_5$ in the general formula (VI) represents a mercapto group.

3. A method of developing a silver halide photographic light-sensitive material as claimed in claim 1, wherein the compound is present in the photographic light-sensitive material.

4. A method of developing a silver halide photographic light-sensitive material as claimed in claim 3, wherein the compound is present in the material in an amount in the range of $1 \times 10^{-5}$ to $1 \times 10^{-1}$ mole per mole of internally-fogged silver halide emulsion.

5. A method of developing a silver halide photographic light-sensitive material as claimed in claim 4, wherein the compound is present in an amount in the range of $1 \times 10^{-4}$ to $1 \times 10^{-2}$ mole per mole of internally-fogged silver halide emulsion.

6. A method of developing a silver halide photographic light-sensitive material as claimed in claim 1, wherein the compound is present in a solution of a developing bath in which the material is being developed or a solution of a prebath of the developing bath.

7. A method of developing a silver halide photographic light-sensitive material as claimed in claim 6, wherein the compound is present in the solution in an amount in the range of from $1 \times 10^{-5}$ to $1 \times 10^{-1}$ mole per liter of solution.

8. A method of developing a silver halide photographic light-sensitive material as claimed in claim 7, wherein the compound is present in the solution in an amount in the range of $1 \times 10^{-4}$ to $1 \times 10^{-2}$ mole per liter of solution.

9. A method of developing a silver halide photographic light-sensitive material as claimed in claim 1, wherein the internally-fogged emulsion includes grains having a mean grain size in the range of 1.0 to 0.05 μm.

10. A method of developing a silver halide photographic light-sensitive material as claimed in claim 9, wherein the internally-fogged emulsion grains have a mean grain size in the range of 0.6 to 0.1 μm.

11. A method of developing a silver halide photographic light-sensitive material as claimed in claim 10, wherein the internally-fogged grains have a mean grain size of 0.5 μm or less.

12. The method according to claim 1, wherein the light-sensitive silver halide emulsion and the internally fogged silver halide emulsion are negative working emulsions.

13. The method according to claim 1, wherein the method further comprises dissolving underdeveloped silver halides of the photographic light-sensitive material and depositing the resulting dissolved silver halides on an image receiving layer provided in the vicinity of the photographic light-sensitive material to provide a positive image.

* * * * *